United States Patent [19]
Adachi

[11] Patent Number: 5,373,358
[45] Date of Patent: Dec. 13, 1994

[54] EXCITATION WAVELENGTH SWEEPING TYPE RAMAN SPECTROSCOPIC APPARATUS

[75] Inventor: Yukio Adachi, Kanagawa, Japan

[73] Assignee: Fuji Xerox Co., Ltd., Tokyo, Japan

[21] Appl. No.: 155,510

[22] Filed: Nov. 22, 1993

Related U.S. Application Data

[63] Continuation-in-part of Ser. No. 932,553, Aug. 20, 1992, abandoned.

[30] Foreign Application Priority Data

Aug. 23, 1991 [JP] Japan .................. 3-235708

[51] Int. Cl.$^5$ .................. G01J 3/44; G01N 21/65
[52] U.S. Cl. .................. 356/301
[58] Field of Search .................. 356/301

[56] References Cited

U.S. PATENT DOCUMENTS

| | | | |
|---|---|---|---|
| 4,648,714 | 3/1987 | Benner et al. | 356/301 |
| 4,907,875 | 3/1990 | Bowley et al. | 356/301 |
| 5,037,200 | 8/1991 | Kodama | 356/301 |
| 5,112,127 | 5/1992 | Carrabba et al. | 356/301 |
| 5,257,085 | 10/1993 | Ulich et al. | 356/301 |

OTHER PUBLICATIONS

Yu, IBM Technical Disclosure Bulletin, vol. 20 No. 10, pp. 4186–4187, Mar. 1978.

Letokhou, Optics and Laser Technology, Jun. 1978 pp. 129–137.

*Primary Examiner*—F. L. Evans
*Attorney, Agent, or Firm*—Finnegan, Henderson, Farabow, Garrett & Dunner

[57] ABSTRACT

An excitation wavelength sweeping type Raman spectroscopic apparatus including a wavelength variable laser source, a laser beam converging unit for irradiating a laser beam from the laser source onto a specimen, a bandpass filter for selecting a beam of a predetermined wavelength out of Raman scattered light beams emitted from the specimen, and a photodetecting unit for detecting the beam selected by the bandpass filter. In the apparatus, a Raman spectrum of the specimen is measured by sweeping the wavelength of the laser beam.

5 Claims, 2 Drawing Sheets

EXCITATION WAVELENGTH SWEEPING TYPE RAMAN SPECTROSCOPIC APPARATUS

REFERENCE TO RELATED APPLICATION

This application is a continuation-in-part of application Ser. No. 07/932,553, filed Aug. 20, 1992, now abandoned.

BACKGROUND OF THE INVENTION

1. Field of the Invention

The invention relates to an excitation wavelength sweeping type Raman spectroscopic apparatus that measures a Raman spectrum of a specimen by sweeping a wavelength of a laser beam.

2. Description of the Related Art

The Raman spectrum, together with an infrared absorption spectrum, is known as a method of measuring a molecular vibration spectrum of gases, liquids, and solids. The Raman spectrum is widely used as a method of evaluating materials.

Raman scattering is a phenomenon in which when monochromatic light (excited light) with a frequency $v_0$ is irradiated onto a material, light of different frequencies ($v_0 \pm v_1$, $v_0 \pm v_2$) is scattered as shown in FIG. 2, other than intense scattered light (Rayleigh scattering) whose frequency is the same as that of the irradiated light. Since a difference ($v_1$, $v_2$ . . . ) between the frequency of the irradiated light and that of the scattered light corresponds principally to the energy difference between the initial state and the final state, Raman spectroscopic apparatuses employed up to now are designed to obtain a Raman spectrum by fixing $v_0$ and dispersing the scattered light with a double monochromator or a triple monochromator.

In these conventional Raman spectroscopic apparatuses, the light obtained by converging the Raman scattered light passes through the entering slit and the exiting slit of the spectroscope to reach the detector, reducing the amount of light to such an extent that the light becomes dark and the transmittance gets impaired. As a result, these conventional spectroscopic apparatuses are not well qualified to detect Raman scattered beams efficiently, nor are they advantageous in that they are heavy and so large that a sufficient space must be provided. In addition these spectroscopic apparatuses are expensive.

Therefore, there has been a demand for developing a highly sensitive Raman spectroscopic apparatus whose efficiency for detecting Raman scattered light is high to replace conventional Raman spectroscopic apparatuses. The invention has been made in view of such a demand.

SUMMARY OF THE INVENTION

An object of the invention is to provide a highly sensitive, small, light, and inexpensive Raman spectroscopic apparatus that can detect Raman scattered light highly efficiently.

In order to attain the above object, the invention provides an excitation wavelength sweeping type Raman spectroscopic apparatus including a wavelength variable laser source, laser beam converging means for irradiating a laser beam from the laser source onto a specimen, a bandpass filter for selecting a beam of a predetermined wavelength out of Raman scattered light beams emitted from the specimen, and photodetecting means for detecting the beam selected by the bandpass filter, wherein a Raman spectrum of the specimen is measured by sweeping a wavelength of the laser beam.

DETAILED DESCRIPTION OF THE PREFERRED EMBODIMENT

An embodiment of the invention will hereunder be described with reference to the accompanying drawings.

Figure 1:
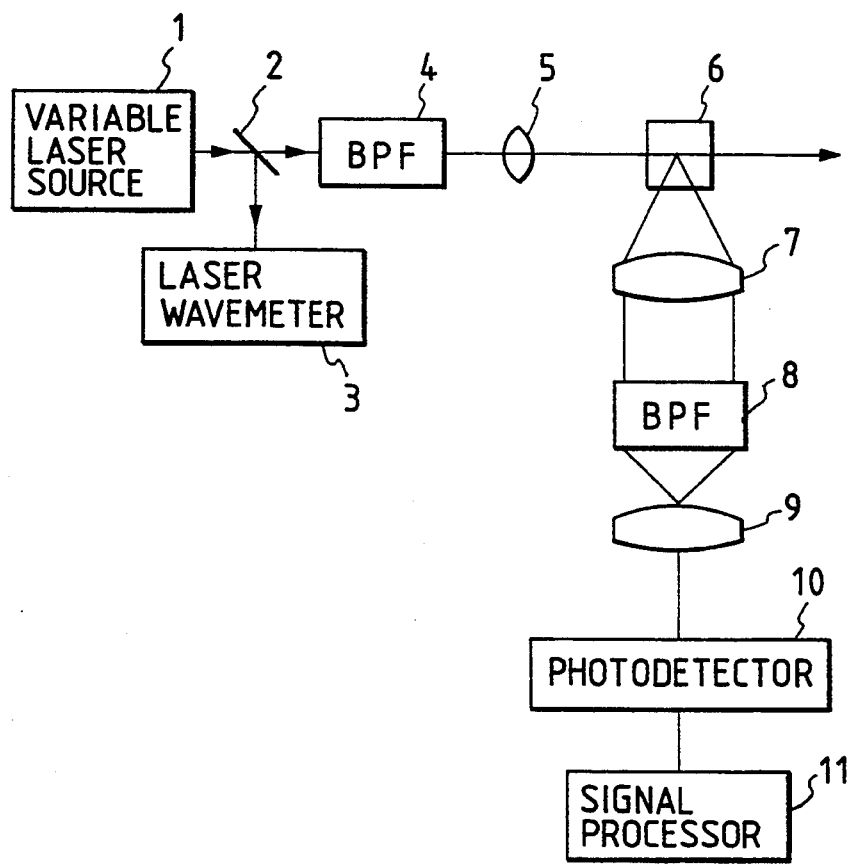
FIG. 1 is a schematic diagram of an excitation wavelength sweeping type Raman spectroscopic apparatus of the invention.
Figure 2:
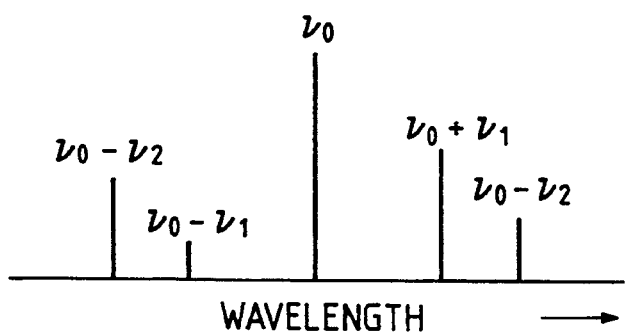
FIG. 2 is a diagram illustrative of scattering of Raman scattered light.

FIG. 1 is a schematic diagram of an excitation wavelength sweeping type Raman spectroscopic apparatus of the invention. The spectroscopic apparatus includes a wavelength variable laser source 1, a laser beam converging system 5, a scattered light converging system 7, a bandpass filter 8, and converging system 9, a photodetector 10, and a signal processor 11.

A part of an output beam from the wavelength variable laser source 1 is split by a beam splitter 2 and guided to a laser wavemeter 3 and a bandpass filter 4. The laser wavemeter 3 may be used when an oscillation wavelength of the wavelength variable laser source 1 is to be measured correctly. Also, the bandpass filter 4 may be used when light that gives measurement background is contained in the wavelength variable laser beams, and noise can thereby be removed.

Figure 3:
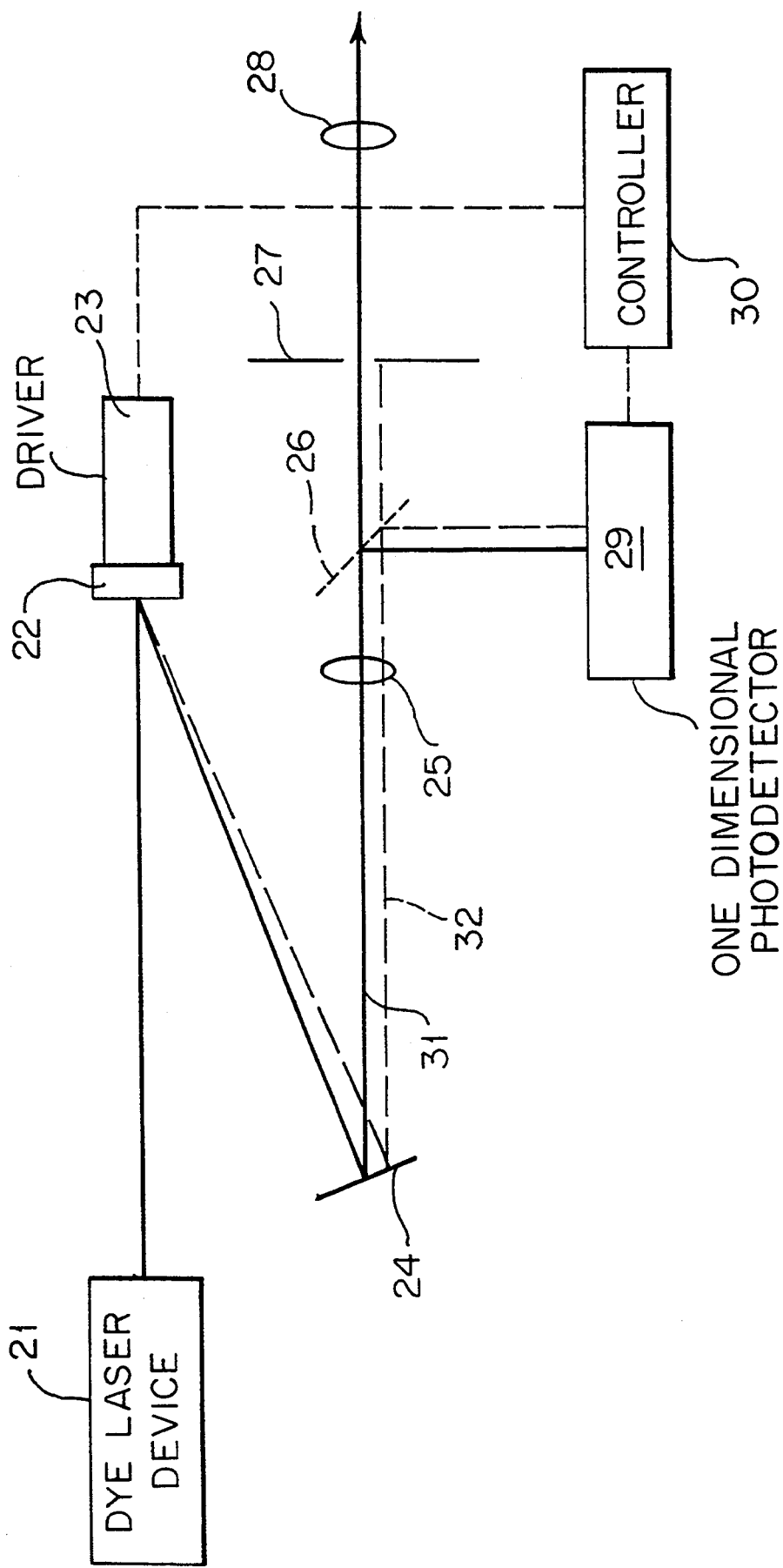
FIG. 3 is a diagram illustrative of the bandpass filter of FIG. 1.

The band pass filter 4 will be described in detail with reference to FIG. 3. In FIG. 3, reference numeral 21 designates a dye laser device which corresponds to the wavelength variable laser source 1 shown in FIG. 1. The dye laser device 21 employs nitrogen laser light or yttrium aluminum garnet (YAG) laser light as excited light, and is able to output a laser light beam having a different wavelength. The bandpass filter 4 in FIG. 1 includes a diffraction grating 22, a driver 23, a mirror 24, a lens 25, a beam splitter 26, a pinhole section 27, a lens 28, a one-dimensional photodetector 29 and a controller 30, as shown in FIG. 3.

The laser light beam having a given wavelength output from the dye laser device 21 is diffracted by the diffraction grating 22 and goes to the mirror 24. The laser beam 31 output from the mirror 24 is converged at the pinhole of the pinhole section 27 by the lens 25, and the components other than the laser beam are removed by the pinhole. Next, the laser beam is collimated by the lens 28 to produce a parallel light beam, which is used as an excited light beam for Raman measurement. On the other hand, the laser beam 31 which passed through the lens 25 is split by the beam splitter 26, and part of the split beam is irradiated onto the one-dimensional photodetector 29. When the wavelength of the light beam from the dye laser device 21 is varied, the diffraction angle of the diffraction grating 22 is varied, so that the path of the laser beam is changed to the position indicated by a broken line 32. As a result, since the position of the laser beam which is detected by the one-dimensional detector 29 is varied, the set angle of the diffraction grating 22 is controlled such that the position of the laser beam at the detector 29 is fixed. That is, the driver 23 is controlled by the controller 30 to change the set angle of the diffraction grating 22, so that the laser beam always passes through the pinhole of the pinhole section 27. Thus, when the wavelength of the laser beam output from the dye laser device 21 is swept, the passing wavelength of the bandpass filter 4 can be varied. Further, since the set angle of the diffraction grating 22 is varied in accordance with the laser wavelength, the wavelength range of passing can be broadened extremely.

The excited laser beam from the bandpass filter 4 irradiates a specimen 6 while being converged by the converging system 5. This causes the Raman scattered light to be radiated efficiently from the specimen 6. The scattered light is converted by the scattered light converging system 7 and the converged light passes through the bandpass filter 8. At this point, the bandpass filter 8 selects only a beam of light of a predetermined wavelength and allows the selected beam to pass therethrough. The beam of light selected by the bandpass filter 8 reaches the photodetector 10 after being converged by the converging system 9. A signal from the photodetector 10 is processed by the signal processor 11.

In the above case, a Raman spectrum of the specimen 6 can be recorded by recording the intensity of a signal from the photodetector 10 while sweeping the oscillation wavelength of the output beam from the wavelength variable laser source 1. Also, the Raman shift can be determined from both the oscillation wavelength of the output beam from the wavelength variable laser source 1 and the central wavelength of the bandpass filter 8.

The resolution of the Raman spectroscopic apparatus of the invention is determined by the linewidth of the excited laser beam and the characteristics of the bandpass filter. However, since the linewidth of the excited laser beam can be narrowed sufficiently, bandpass filters of different characteristics may be used by additionally providing a mechanism for changing one bandpass filter with another. This will make the resolution of the Raman spectroscopic apparatus variable.

Further, if the range of varying the wavelength of the wavelength variable laser beam is so narrow that measurements over a wide range cannot be made, a mechanism for changing bandpass filters of different central frequencies may be additionally provided, so that the measurable range can be increased.

The excitation wavelength sweeping type Raman spectroscopic apparatus of the invention has the following advantages compared with the conventional Raman spectroscopic apparatuses.

Since the bandpass filter is bright and has a high transparency, the Raman scattered light can be detected efficiently. Further, since the bandpass filter is small, light, and inexpensive, a small, light and inexpensive Raman spectroscopic apparatus can be fabricated.

The absence of an entering slit allows the Raman scattered light from a wide region to be detected efficiently.

Even if the resolution is improved by narrowing the linewidth of an excited laser beam, the bandpass filter, whose transmittance is not impaired compared with a spectroscope, can be used for measurements at high resolutions.

Since the wavelength of scattered light to be detected is constant, the optical systems such as the converging system can be designed easily. In addition, the Raman shift can be determined correctly by measuring the wavelength of an excited laser beam.

Since the wavelength of scattered light to be detected is constant, the sensitivity of the detecting system remains unchanged. Therefore, the sensitivity of the Raman spectrum can be corrected easily by measuring the output of a laser source.

What is claimed is:

1. An excitation wavelength sweeping type Raman spectroscopic apparatus comprising:
   a wavelength variable laser source;
   a first bandpass filter for removing noise from a laser beam emitted by said laser source, a passing wavelength of said first bandpass filter being variable;
   laser beam converging means for irradiating the laser beam passed by said first bandpass filter onto a specimen;
   a second bandpass filter for selecting a beam of a predetermined wavelength out of Raman scattered light beams emitted from the specimen; and
   photodetecting means for detecting the beam selected by said second bandpass filter,
   wherein a Raman spectrum of the specimen is measured by sweeping the wavelength of said laser beam and varying the passing wavelength of said first bandpass filter.

2. The apparatus according to claim 1, further comprising a laser wavemeter for measuring the wavelength of said laser beam.

3. The apparatus according to claim 1, further comprising converging means for converging the Raman scattered light beams emitted from the specimen and for supplying converged beams to said second bandpass filter.

4. The apparatus according to claim 1, further comprising converging means for converging the beam selected by said second bandpass filter and for supplying a converged beam to said photodetecting means.

5. The apparatus according to claim 1, further comprising a signal processor for processing a signal from said photodetecting means.

* * * * *